(12) United States Patent
Kim et al.

(10) Patent No.: US 11,229,582 B2
(45) Date of Patent: *Jan. 25, 2022

(54) PATCH FOR TOOTH ATTACHMENT ABLE TO BE REMOVED BY TOOTH BRUSHING

(71) Applicant: LG Household & Health Care Ltd., Seoul (KR)

(72) Inventors: Jong-Hoon Kim, Daejeon (KR); Jae-Hyun Ahn, Daejeon (KR); Kwang-Ho Oh, Daejeon (KR); In-Ho Lee, Daejeon (KR); Woo-Sun Shim, Daejeon (KR)

(73) Assignee: LG Household & Health Care Ltd.

( * ) Notice: Subject to any disclaimer, the term of this patent is extended or adjusted under 35 U.S.C. 154(b) by 130 days.

This patent is subject to a terminal disclaimer.

(21) Appl. No.: 15/766,182

(22) PCT Filed: Aug. 30, 2016

(86) PCT No.: PCT/KR2016/009666
§ 371 (c)(1),
(2) Date: Apr. 5, 2018

(87) PCT Pub. No.: WO2017/061699
PCT Pub. Date: Apr. 13, 2017

(65) Prior Publication Data
US 2018/0289594 A1    Oct. 11, 2018

(30) Foreign Application Priority Data

Oct. 6, 2015    (KR) .......................... 10-2015-0140104
Oct. 21, 2015   (KR) .......................... 10-2015-0146678
Oct. 28, 2015   (KR) .......................... 10-2015-0150249
Nov. 10, 2015   (KR) .......................... 10-2015-0157626

(51) Int. Cl.
| | |
|---|---|
| A61K 8/02 | (2006.01) |
| A61K 8/22 | (2006.01) |
| A61K 8/24 | (2006.01) |
| A61K 8/97 | (2017.01) |
| A61Q 11/02 | (2006.01) |
| A61K 8/72 | (2006.01) |
| A61K 8/19 | (2006.01) |
| A61K 47/38 | (2006.01) |
| A61K 9/70 | (2006.01) |
| A61K 9/00 | (2006.01) |
| A61K 47/32 | (2006.01) |
| A61K 33/40 | (2006.01) |
| A61K 8/34 | (2006.01) |
| A61K 8/49 | (2006.01) |
| A61K 8/73 | (2006.01) |
| A61K 8/81 | (2006.01) |
| A61K 8/92 | (2006.01) |
| A61Q 11/00 | (2006.01) |
| A61K 8/9794 | (2017.01) |
| A61K 8/9789 | (2017.01) |

(52) U.S. Cl.
CPC .............. *A61K 8/0208* (2013.01); *A61K 8/02* (2013.01); *A61K 8/19* (2013.01); *A61K 8/22* (2013.01); *A61K 8/24* (2013.01); *A61K 8/34* (2013.01); *A61K 8/345* (2013.01); *A61K 8/4973* (2013.01); *A61K 8/72* (2013.01); *A61K 8/73* (2013.01); *A61K 8/731* (2013.01); *A61K 8/8176* (2013.01); *A61K 8/922* (2013.01); *A61K 8/97* (2013.01); *A61K 8/9789* (2017.08); *A61K 8/9794* (2017.08); *A61K 9/006* (2013.01); *A61K 9/0056* (2013.01); *A61K 9/0063* (2013.01); *A61K 9/7007* (2013.01); *A61K 9/7053* (2013.01); *A61K 33/40* (2013.01); *A61K 47/32* (2013.01); *A61K 47/38* (2013.01); *A61Q 11/00* (2013.01); *A61Q 11/02* (2013.01); *A61K 2800/92* (2013.01)

(58) Field of Classification Search
CPC ..................................... A61K 8/73; A61K 8/22
USPC ........................................................... 424/53
See application file for complete search history.

(56) References Cited

U.S. PATENT DOCUMENTS

| | | | |
|---|---|---|---|
| 6,375,963 B1 | 4/2002 | Repka et al. | |
| 6,669,929 B1 * | 12/2003 | Boyd ..................... | A61K 8/042 424/49 |
| 6,682,721 B2 | 1/2004 | Kim et al. | |
| 6,689,344 B2 | 2/2004 | Chang et al. | |
| 6,780,401 B2 | 8/2004 | Kim et al. | |
| 2003/0124178 A1 | 7/2003 | Haley | |
| 2003/0194382 A1 | 10/2003 | Chang et al. | |
| 2004/0028732 A1 | 2/2004 | Falkenhausen et al. | |
| 2004/0033205 A1 | 2/2004 | Date et al. | |
| 2004/0057910 A1 | 3/2004 | Lee et al. | |
| 2004/0180080 A1 | 9/2004 | Furusawa et al. | |

(Continued)

FOREIGN PATENT DOCUMENTS

| | | |
|---|---|---|
| CN | 1720916 A | 1/2006 |
| CN | 101371817 A | 2/2009 |

(Continued)

OTHER PUBLICATIONS

Search report from International Application No. PCT/KR2016/009662, dated Jan. 11, 2017.

(Continued)

*Primary Examiner* — Walter E Webb
(74) *Attorney, Agent, or Firm* — Lerner, David, Littenberg, Krumholz & Mentlik, LLP

(57) ABSTRACT

The present invention provides a patch for attaching to teeth or a surrounding part of teeth, and the patch can be easily removed by tooth brushing alone.

20 Claims, 8 Drawing Sheets

(56) References Cited

U.S. PATENT DOCUMENTS

| | | |
|---|---|---|
| 2004/0219113 A1 | 11/2004 | Choi et al. |
| 2005/0232982 A1 | 10/2005 | Ihara et al. |
| 2006/0018845 A1* | 1/2006 | Edelstein ............ A61K 8/0208 424/53 |
| 2006/0073174 A1 | 4/2006 | Moro et al. |
| 2006/0099550 A1* | 5/2006 | Faasse ................ A61C 19/063 433/215 |
| 2012/0100192 A1 | 4/2012 | Penhasi et al. |
| 2013/0011449 A1 | 1/2013 | Tomioka et al. |
| 2014/0314692 A1 | 10/2014 | Vaccaro et al. |
| 2018/0250203 A1 | 9/2018 | Kim et al. |

FOREIGN PATENT DOCUMENTS

| | | |
|---|---|---|
| CN | 104013536 A | 9/2014 |
| CN | 203915531 U | 11/2014 |
| EP | 2113238 A1 | 11/2009 |
| JP | 2004501958 A | 1/2004 |
| JP | 2006505614 A | 2/2006 |
| JP | 2015101566 A | 6/2015 |
| KR | 20030031511 A | 4/2003 |
| KR | 20040000784 A | 1/2004 |
| KR | 100440241 B1 | 7/2004 |
| KR | 100458337 B1 | 12/2004 |
| KR | 20050072086 A | 7/2005 |
| KR | 20050082187 A | 8/2005 |
| KR | 20050119914 A | 12/2005 |
| KR | 20060094713 A | 8/2006 |
| KR | 20060097172 A | 9/2006 |
| KR | 20060097177 A | 9/2006 |
| KR | 100648022 B1 | 11/2006 |
| KR | 100755765 B1 | 9/2007 |
| KR | 100816250 B1 | 3/2008 |
| KR | 101148470 B1 | 5/2012 |
| KR | 20150111667 A | 10/2015 |
| KR | 20150118784 A | 10/2015 |
| TW | 201713318 A | 4/2017 |
| WO | 2002074275 A2 | 9/2002 |
| WO | 2011118454 A1 | 9/2011 |
| WO | WO2013/039495 * | 3/2013 ............... A61K 8/02 |

OTHER PUBLICATIONS

Search report from International Application No. PCT/KR2016/009666, dated Dec. 13, 2016.

Extended European Search Report for Application No. EP16844620.1 dated Mar. 28, 2019.

Taiwanese Search Report for Application No. TW105128830, dated Jul. 15, 2020, 1 page.

Chinese Search Report for Application No. 201680052028.7, dated Aug. 14, 2020, pp. 1-3.

* cited by examiner (a)  (b)

PATCH FOR TOOTH ATTACHMENT ABLE TO BE REMOVED BY TOOTH BRUSHING

CROSS-REFERENCE TO RELATED APPLICATIONS

The present application is a national phase entry under 35 U.S.C. § 371 of International Application No. PCT/KR2016/009666, filed on Aug. 30, 2016, which claims priority to Korean Patent Application No. 10-2015-0140104, filed on Oct. 6, 2015, Korean Patent Application No. 10-2015-0157626, filed on Nov. 10, 2015, Korean Patent Application No. 10-2015-0146678, filed on Oct. 21, 2015, and Korean Patent Application No. 10-2015-0150249, filed on Oct. 28, 2015 in the Republic of Korea, the disclosures of which are incorporated herein by reference.

TECHNICAL FIELD

The present invention relates to a tooth-attachable patch capable of being removed by tooth brushing, and more specifically, it relates to a tooth-attachable patch which can be simply removed by external force such as tooth brushing without stripping off a backing layer supporting a drug layer.

BACKGROUND ART

Procedures such as whitening of teeth have been performed mainly in dentistry in the past, but since dental procedures are cumbersome and very expensive, there have been a lot of developments in recent years for easy-to-use products.

There are products such as toothpaste, mouth rinse, chewing gum, oral tray, gel for tooth application, and mouth patch for selection of teeth whitening, but patch type products are used most in consideration of convenience of use.

A tooth-attachable patch generally has a structure including a drug layer containing a drug for the purpose of use, such as a drug for tooth whitening, a drug for preventing or improving sensitive teeth, and a backing layer for selectively delivering the drug component to teeth.

Korean Patent No. 10-0458337 suggests manufacturing the backing layer to be water-insoluble, so as to selectively deliver the drug component contained in the patch only to teeth. However, the patch including such water-insoluble backing layer is cumbersome to remove the remaining backing layer after use. As a product improving this problem, a product which is dissolved in the oral cavity after patch attachment was developed, but the drug component was not selectively delivered to teeth and mixed with saliva, resulting in the problem that the intended drug effect was not expressed.

Meanwhile, if the patch is removed by tooth brushing alone without stripping off the patch, the undegraded film lumps will become clogged in a toothbrush, making it difficult to remove it from the toothbrush. As a product improving this problem, a product which is dissolved in the oral cavity after patch attachment was developed, but the drug component was not selectively delivered to teeth and mixed with saliva, resulting in the problem that the intended drug effect was not expressed. And, there is a problem of ingesting efficacious substance, and also there is a problem that the drug melts out from an outer layer not from a tooth attaching part and therefore the drug contained in the outer layer is not adequately supplied to teeth.

In the method of tearing off a patch after use, there are many cases where residue is left due to adhesive force between teeth and a patch, and in some cases, the patch is broken during removal depending on tensile force of the patch. The inventors of the present invention have studied how to easily remove the patch by simple methods such as tooth brushing, thereby completing the present invention.

DISCLOSURE

Technical Problem

The present invention is directed to providing a convenient patch for attaching to teeth or a surrounding part of teeth, which can be simply removed by tooth brushing alone without generation of a separate waste after use.

Further, the present invention is directed to providing a patch, in which a water-insoluble polymer prevents a drug from being released to the outside during use, so that the drug can be properly supplied to the target site, and a water-soluble polymer absorbs saliva thereby loosening the bonds between the polymers formed in the backing layer over time; and therefore, the patch may be easily removed by physical removal methods such as tooth brushing.

Meanwhile, in order to solve the above problem, the present invention is directed to providing a patch for attaching to teeth or a surrounding tissue of teeth capable of being easily removed from the surface of teeth by tooth brushing alone.

Further, the present invention is directed to providing a patch for attaching to teeth or a surrounding tissue of teeth capable of being easily degraded or removed by tooth brushing, which has especially excellent removability and provides excellent use sensation without foreign body sensation due to small size of disassembled particles.

These and other objects and advantages of the present invention may be understood from the following detailed description and will become more fully apparent from the exemplary embodiments of the present invention. Also, it will be easily understood that the objects and advantages of the present invention may be realized by the means shown in the appended claims and combinations thereof.

Technical Solution

In order to achieve the above objects, the present invention recognized that a backing layer of a patch for attaching to teeth or a surrounding part of teeth, which allows a drug contained in a tooth-attachable patch to selectively move to the surface of teeth and plays a role in maintain the shape of the patch uniformly, is cumbersome to be removed after use, and it has been studied for a long time to provide a method for conveniently removing the backing layer by tooth brushing alone, thereby completing the present invention.

The inventors of the present invention have confirmed from several experiments that there is a difference in removability of the patches attached to the surface of teeth according to the change in tensile strength measured after use.

Namely, it was found that, after a drug contained in a drug layer of the patch for attaching to teeth or a surrounding part of teeth is released to the surface of teeth, tensile strength of the backing layer remaining on the surface of teeth is controlled to remove the backing layer only by tooth brushing without having to strip off it by hand.

One embodiment of the present invention provides a patch for attaching to teeth or a surrounding part of teeth, which comprises: a drug layer including a drug component; and a backing layer which is positioned on one side of the drug layer and whose tensile strength is reduced by 50% or more by absorbing moisture, compared to before moisture absorption.

The patch for attaching to teeth or a surrounding part of teeth can be degraded and removed by tooth brushing.

The tensile strength of the backing layer according to one embodiment of the present invention, which is measured in a state that moisture is sufficiently absorbed, may be reduced by 50% or more, compared to before moisture absorption. The state that moisture is sufficiently absorbed may mean a degree of substantially no change in moisture content rate even if moisture is continuously supplied. It can be understood that a degree of evaporation into the air does not substantially change the moisture content rate.

The tensile strength of the backing layer may be reduced by 60% or more, compared to before moisture absorption, and it may be reduced by preferably 60% to 95%.

Preferably, the tensile strength of the backing layer of the present invention, which is measured in a state that moisture is sufficiently absorbed so that the moisture content rate does not change for 10 sec, may be reduced by 50% or more, compared to before moisture absorption. Specifically, the tensile strength of the backing layer, which is measured at an environment of temperature of 25° C. using Zwick, DE/1494 universal testing machine at a rate of 0.1 mm/s, may be reduced by 50% or more, compared to before moisture absorption.

According to one embodiment of the present invention, when the tensile strength is reduced by 50% or more, compared to before contact to moisture, degradation of the backing layer of the patch may become easy. Also, it may be easy to strip the degraded backing layer of the patch off. In another embodiment of the present invention, when the tensile strength is reduced by 50% or more, degree to which the backing layer is degraded and removed by tooth brushing is observed to be excellent.

The patch of the present invention comprising the drug layer and the backing layer can be used by attaching to teeth. In another embodiment, the patch can be used by attaching to teeth or a surrounding tissue of teeth depending on the purpose of the patch. The term "surrounding part or surrounding tissue of teeth" used herein may include both the portion of the gum that is in contact with teeth and the portion of the oral cavity that may be in contact with a tooth brush in the course of tooth brushing, even though the portion is somewhat apart from teeth.

The term "degradation" means that one large piece is divided into smaller pieces or split apart. The disassembled pieces of the present invention may have a certain size, but may be divided into various sizes depending on external force or pressure.

The term "stripping off" means a state in which at least a part of the patch is separated from the surface of teeth unlike a state in which the patch is attached to the surface of teeth, and means a state in which a part of the patch falls naturally by external force applied to the surface of teeth or as time goes on.

The term "tooth brushing" used herein is also called brushing, and means a process of removing residues left in the surface of teeth or foreign matters in the gap of teeth by applying force perpendicular or parallel to the surface of teeth.

The term "tensile strength" means the value applied to a material until the material gradually stretches when a material is pulled by applying force and finally broken or fractured. The term "tensile strength" used herein means the force at which a tooth-attachable patch with length of 1 cm and width of 7 cm, respectively, is finally broken by pulling the patch in the longitudinal direction.

In particular, the inventors of the present invention was confirmed the fact that tensile strength required for achieving the object of the present invention can be achieved by the combination of a water-soluble polymer and a water-insoluble polymer contained in the backing layer.

The tooth-attachable patch of the present invention may comprise a drug layer including a drug component and a backing layer positioned on the opposite side of the side where the drug layer is attached to the surface of teeth.

Most patch-type drug delivery systems, especially tooth-attachable patches, are equipped with a backing layer to allow specific drug delivery to the target site. In general, the backing layer is made of a polymer that is not soluble in moisture or saliva and can maintain its shape even when attached to the teeth. And, when the medicinal ingredients are released and delivered to teeth after being attached to teeth, the backing layer make the medicinal ingredients be released only in the direction of teeth. Namely, it was common to produce the backing layer water-impermeable or water-insoluble in order to selectively deliver the drug in the direction of teeth and prevent the drug from diluting with saliva or water.

Such water-impermeable or water-insoluble backing layer had to be stripped off from the surface of teeth after using the patch.

After removing the backing layer after use, in order to remove the residue remained in the surface of teeth, teeth should be brushed. Accordingly, the inventors of the present invention provide a method for adjusting tensile strength of the backing layer so as to conveniently remove the backing layer from the surface of teeth by only tooth brushing while transferring the drug to the surface of teeth without removing the backing layer.

Namely, the drug backing layer, which was only made water-insoluble and was being used for a while in the art, was manufactured in the form that can be degraded by tooth brushing by controlling tensile strength, without stripping off the backing layer.

The drug layer may include drugs to be delivered to teeth. The drugs may preferably be delivered to the surface of teeth, and examples of the drugs may include ingredients for whitening teeth, ingredients for preventing or improving sensitive teeth, ingredients for preventing or improving periodontitis, ingredients for preventing or improving gingivitis, or ingredients for preventing cavities.

The ingredients for whitening teeth may be peroxides, polyphosphates, enzymes, chlorinated bleaching agents. The peroxides may be selected from the group consisting of hydrogen peroxide, carbamide peroxide, calcium peroxide, sodium percarbonate, sodium perborate, tetrasodium pyrophosphate peroxidate and a mixture thereof. The phosphates and the enzymes are effective for removing major stains contained in an enamel layer. The polyphosphates may be, for example, at least one selected from the group consisting of tetrasodium pyrophosphate (TSPP), sodium acid pyrophosphate (SAPP), sodium hexametaphosphate (SHMP), sodium tripolyphosphate (STP), sodium potassium tripolyphosphate (SKTP), tetrapotassium pyrophosphate (TKPP), ultra-metaphosphate (acidic sodium meta-polyphosphate) as ultra-phosphate and acidic sodium polyphosphate. In general, polyphosphate is a tartar controlling agent in a toothpaste and known to be effective in inhibiting tartar formation and tartar removal in toothpaste. Further, the polyphosphate is a good metal chelating agent and therefore it can effectively remove tooth stains, especially, formed by metal in foods or working environment such as iron, calcium and magnesium, thereby somewhat contributing to enhance whitening effect. When using the polyphosphate in the preparation according to the present invention, it is expected that not only improvement of whitening effect by removal of light extrinsic stain but also prolongation of contact time between teeth and condensed phosphate is effective in inhibiting tartar formation and tartar removal. The chlorinated bleaching agents may be sodium chlorite, sodium hypochlorite and the like. In addition, papain, vitamin E and sodium bicarbonate also can be used as a whitener.

In another embodiment, the ingredients for preventing or improving sensitive teeth, or preventing cavities may be strontium chloride, calcium carbonate, sodium citrate, sodium fluoride, silica, hydroxyapatite, potassium nitrate, potassium phosphate and the like.

In another embodiment, the drug component may include ingredients for preventing periodontal disease, and the periodontal disease refers to the loss of teeth due to periodontitis, gingivitis and hemorrhage, formation of periodontal pockets, and destruction of alveolar bone. In order to prevent the incidence of the periodontal disease, the drug layer may include bamboo salt, titrated Extract of *Zea Mays* L. unsaponifiable fraction, policresulen, tetracycline, chlorhexidine gluconate, cetyl pyridinium chloride, sanguinarine, triclosan and the like, and also include an extract of herbal medicine such as *Magnoliae* Cortex, *Centella Asiatica, Chamomile, Rhatany,* Myrrha, Mori Cortex Radicis, *Cimicifugae Rhizoma*, Green tea, *Glycyrrhizae* Radix et Rhizoma, *Scutellariae* Radix, Taraxaci Herba, and *Lonicerae Flos*.

The drug layer is preferably a dry type in which the drug layer has no or weak adhesion strength in a dry condition, but when it is hydrated by a small amount of water at the site where the whitener is desired to function, it begins to have adhesion strength and to release the whitener as it begins to be hydrated. However, it can also be used as a gel type that can be attached to teeth by its own viscosity. The polymer which can be used in the drug layer should have hydrophilicity or at least partial hydrophilicity. The polymer typically used may be polyalkyl vinyl ether-maleic acid copolymer (PVM/MA copolymer; Gantrez AN 119, AN 139, S-97), polyvinyl alcohol, polyacrylic acid, Poloxamer 407 (Pluronic, poly(ethylene oxide)-poly(propylene oxide)-poly (ethylene oxide) triblock copolymer), polyethyleneoxide (Polyox), polyvinyl pyrrolidone-vinyl acetate copolymer (PVP/VA copolymer; Luviskol VA, Plasdone S PVP/VA), polyvinyl pyrrolidone (PVP; K-15~K-120), polyquaternium-11 (Gafquat 755N), polyquaternium-39 (Merquat plus 3330), carboxypolymethylene (Carbomer, Carbopol), hydroxypropyl methyl cellulose, hydroxyethyl cellulose, hydroxypropyl cellulose, gelatin, sodium alginate alone or a mixture thereof. A solvent for the polymer may be primarily water, ethanol alone or a mixture thereof, and other organic solvents, for example, ethyl acetate, methylene chloride, isopropyl alcohol, acetonitrile alone or a mixture thereof at a controlled ratio.

A matter for tooth attachment should be flexible enough to be attached directly to teeth and be easily shaped according to the flexion of teeth. Depending on the polymer, this flexibility may be poor, so a suitable plasticizer may be added. Suitable plasticizer may vary depending on the kind of polymer and its prescription, and polypropylene glycol, glycerin or polyethylene glycol is generally used, and all of them also can be used.

Further, in the drug layer, a chelating agent such as EDTA or sodium citrate may be added for the purpose of improving the temporal stability of peroxide.

The term "drug layer" used herein means a layer containing medicinal ingredients to achieve the goal of a tooth-attachable patch. For example, a patch for tooth whitening means a layer containing tooth whitening ingredients (preferably, hydrogen peroxide, sodium peroxide and the like), and a patch for relieving sensitive teeth means a layer containing ingredients for relieving sensitive teeth such as potassium nitrate, potassium chloride and the like.

The term "backing layer" used herein may play a role in preventing contact of the drug layer with the skin in the oral cavity other than teeth.

In one embodiment of the present invention, the backing layer may include a water-insoluble polymer generally used in an oral film, and for example, it may be some of cellulose acetate phthalate, shellac, polyvinyl acetate, ethyl cellulose, polymethyl methacrylate, methacryloyl ethyl betaine/methacrylate copolymer (Yukaformer: manufactured by Mitsubishi), methacrylic acid copolymer (Eudragit L 100, Eudragit L 12,5, Eudragit L 100-55, Eudragit L 30D-55), aminoalkyl methacrylate copolymer (Eudragit E 100, Eudragit E 12,5, Eudragit RL 100, Eudragit RL 30D) and the like. In addition, the backing layer of the patch for attaching to teeth of the present invention includes a water-soluble polymer. The term "water-soluble polymer" used herein means a polymer which can be dissolved in water, swelled or dispersed into small particles. A hydrophilic polymer also can be in the same meaning as the water-soluble polymer of the present invention.

The water-soluble polymer may include a water-soluble polymer which can be used in a drug layer. It may be polyalkyl vinyl ether-maleic acid copolymer (PVM/MA copolymer; Gantrez AN 119, AN 139, S-97), polyvinyl alcohol, polyacrylic acid, Poloxamer 407 (Pluronic, poly (ethylene oxide)-poly(propylene oxide)-poly(ethylene oxide) triblock copolymer), polyethyleneoxide (Polyox), polyvinyl pyrrolidone-vinylacetate copolymer (PVP/VA copolymer; Luviskol VA, Plasdone S PVP/VA), polyvinyl pyrrolidone (PVP; K-15~K-120), polyquaternium-11 (Gafquat 755N), polyquaternium-39 (Merquat plus 3330), carboxypolymethylene (Carbomer, Carbopol), hydroxypropyl methyl cellulose, hydroxyethyl cellulose, hydroxypropyl cellulose, gelatin, sodium alginate and the like, and preferably, it may be hydroxypropyl methyl cellulose, polyvinyl pyrrolidone or a mixture thereof.

The backing layer can be added with various plasticizers for the same reasons as the drug layer. In addition to the above-mentioned plasticizers, propylene glycol, glycerin and polyethylene glycol, more kinds of plasticizers can be used depending on the solvent used, and castor oil and hydrogenated castor oil can also be used.

A solvent for the polymer may be primarily water, ethanol alone or a mixture thereof, and other organic solvents, for example, ethyl acetate, methylene chloride, isopropyl alcohol, acetonitrile alone or a mixture thereof at a controlled ratio.

According to one embodiment of the present invention, a weight ratio of the water-soluble polymer and the water-insoluble polymer included in the backing layer (water-soluble polymer:water-insoluble polymer) may be 1:4 to 4:1, preferably 1.5:4 to 3.5:4.

When the water-soluble polymer and the water-insoluble polymer are in the above-mentioned weight ratio, the patch backing layer of the present invention can be easily removed by tooth brushing after moisture absorption while stably supporting the drug layer.

If the amount of the water-soluble polymer is excessive, there are shortcomings that the backing layer may not function properly and may have week shape fixing force of the patch. If the amount of the water-soluble polymer is small, it may be difficult to achieve the object of the present invention since tensile strength change rate after moisture absorption is low and degree of degradation of the patch by brushing is low.

In addition to the drug layer and the backing layer, the patch for attaching to teeth of the present invention may selectively further include a layer between the drug layer and the backing layer or each of the outside of the layers depending on the purpose.

According to one embodiment of the present invention, the patch for attaching to teeth of the present invention can be easily removed from teeth by tooth brushing alone after use, without stripping off the backing layer separately.

The tooth-attachable patch of the present invention can be easily removed by brushing alone after use.

The term "patch" used herein means an attachable-type formulation containing a specific component, and the shape or structure of the patch is not particularly limited.

Further, the tooth-attachable patch according to the present invention can be manufactured in accordance with the methods disclosed in U.S. Pat. Nos. 6,689,344, 6,682,721, 6,780,401 and the like.

According to another embodiment of the present invention, it was confirmed that, when the backing layer of the patch attachable to the oral cavity has static contact angle variation over time, the backing layer prevents the drug from being released to the outside during use so that the drug can be properly supplied to the target site; the portion, where the backing layer is in contact with saliva, can absorb the saliva thereby loosening the bonds between the polymers formed in the backing layer over time; and therefore, the backing layer may be easily removed by physical removal methods such as tooth.

The inventors of the present invention found the fact that contact angle variation of the backing layer is important to achieve the object of the present invention. In particular, the inventors of the present invention found that, when the static contact angle variation is within a certain range, the original purpose of the backing layer of a tooth-attachable patch can be achieved, and also the backing layer can be easily removed by tooth brushing.

"Contact angle" refers to the angle formed when liquid and gas equilibrate thermodynamically on the solid surface. The term "contact angle" used herein is a measure of wettability of the solid surface and measured mostly by sessile drop. The low contact angle means high wettability and high contact angle means low wettability. Unit can be expressed in ° (degree).

The types of contact angle include static contact angle and dynamic contact angle, and the contact angle used herein may mean static contact angle.

According to one embodiment of the present invention, the present invention provides a patch for attaching to teeth or a surrounding tissue of teeth, which comprises: a drug layer attached to teeth or a surrounding tissue of teeth; and a backing layer which is positioned on one side of the drug layer and has static contact angle variation over time.

Preferably, when static contact angle variation, which is changed between 10 sec to 300 sec after dropping water on the backing layer of the patch, is with a range from 13° to 50°, the patch can be easily degraded and removed by external force such as tooth brushing.

The static contact angle variation of the backing layer of the patch, measured at a temperature of 20° C. for 10 sec to 300 sec, may be 13° to 50°, and preferably, humidity may be humidity ay normal laboratory condition (about 20° C.).

After research for a long time, the inventors of the present invention confirmed the fact that, when the backing layer of the patch has contact angle within the above range, excellent removability and excellent use sensation due to less foreign body sensation after brushing can provided.

The patch is not dissolved in the oral cavity by saliva or moisture, and can be degraded and removed by tooth brushing.

In the patch having static contact angle variation within a range from 13° to 50°, which is changed between 10 sec to 300 sec after dropping water on the backing layer of the patch, "degradation" means that one large piece is divided into smaller pieces or split apart. The disassembled pieces of the present invention may have a certain size, but may be divided into various sizes depending on external force or pressure. If a word has the meaning of being divided into several parts, it can be included in the scope of identity with the "degradation" of the present invention.

For example, after brushing the patch for 3 min at a rate of 90 time per min back and forth at a load of 250 g, collecting wash solution while washing the patch with distilled water, filtering the collected solution through a 1 mm-mesh sieve, and then drying the residue, the substantially degraded backing layer of the patch may have a dry weight of the residue of just less than 5 wt %, preferably less than 4.5 wt % and more preferably less than 4 wt %, based on the total weight of the patch.

In another embodiment of the present invention, it was confirmed that the backing layer, which is positioned on one side of the drug layer in contact with teeth or a surrounding tissue of teeth, has an influence on the characteristics of the backing layer according to solubility parameter of the polymer included in the backing layer.

Specifically, after research for a long time, it was confirmed that it is important that the polymer for forming the backing layer contained in the backing layer has a solubility parameter value within a certain range in order to allow the backing layer of the patch to be degraded by external force such as tooth brushing.

The backing layer may be formed by including both of a polymer having solubility parameter ($\delta1$) of 5 $(MPa)^{1/2}$ to 22 $(MPa)^{1/2}$ and a polymer having solubility parameter ($\delta2$) of 23.5 $(MPa)^{1/2}$ to 40 $(MPa)^{1/2}$.

The inventors of the present invention confirmed that the backing layer prevents the drug from being released to the outside during use, so that the drug can be properly supplied to the target site, and the portion, where the backing layer is in contact with saliva, can absorb the saliva over time and therefore the backing layer may be easily removed by physical removal methods such as tooth brushing. It is considered that the backing layer is degraded by loosening the bonds between the polymers formed in the backing layer, but it is not necessarily interpreted to be limited to such theoretical background.

The term "solubility parameter ($\delta$)" used herein means one index of solubility that expresses solubility in numerical values, and is the square root of the value obtained by dividing the intermolecular cohesive energy by its molecular volume and is expressed by the following Formula 1. Unit is $(MPa)^{1/2}$.

$$\delta = (E/V)^{1/2} \quad \text{[Formula 1]}$$

wherein, E is intermolecular cohesive energy, and V is molecular volume.

Herein, the solubility parameter can be represented using the calculated values based on the solubility parameter of Hansen [See: Handbook of Solubility Parameters and other cohesion parameters, A. Barton ed., CRC Press, Boca Raton Fla., 1985].

After research for a long time, the inventors of the present invention confirmed the fact that, when the backing layer of the tooth attachable patch is formed to include both of the polymer having solubility parameter ($\delta 1$) of 5 $(MPa)^{1/2}$ to 22 $(MPa)^{1/2}$ and the polymer having solubility parameter ($\delta 2$) of 23.5 $(MPa)^{1/2}$ to 40 $(MPa)^{1/2}$, excellent degradation ability by tooth brushing and excellent use sensation due to less foreign body sensation after brushing can provided.

In one embodiment of the present invention, the polymer having solubility parameter ($\delta 1$) of 5 $(MPa)^{1/2}$ to 22 $(MPa)^{1/2}$ of the backing layer may be cellulose acetate phthalate, shellac, polyvinyl acetate, ethyl cellulose, polymethyl methacrylate, methacryloyl ethyl betaine/methacrylate copolymer (Yukaformer: manufactured by Mitsubishi), methacrylic acid copolymer (Eudragit L 100, Eudragit L 12,5, Eudragit L 100-55, Eudragit L 30D-55), aminoalkyl methacrylate copolymer (Eudragit E 100, Eudragit E 12,5, Eudragit RL 100, Eudragit RL 30D) and the like.

Preferably, the polymer having solubility parameter ($\delta 1$) of 5 $(MPa)^{1/2}$ to 22 $(MPa)^{1/2}$ may be ethyl cellulose to achieve the object of the present invention.

The backing layer of the tooth attachable patch of the present invention, which can be removed by tooth brushing, uses the polymer having solubility parameter ($\delta 1$) of 5 $(MPa)^{1/2}$ to 22 $(MPa)^{1/2}$ and a polymer having solubility parameter ($\delta 2$) of 23.5 $(MPa)^{1/2}$ to 40 $(MPa)^{1/2}$ together. The polymer having solubility parameter ($\delta 2$) of 23.5 $(MPa)^{1/2}$ to 40 $(MPa)^{1/2}$ may be polyalkyl vinyl ether-maleic acid copolymer (PVM/MA copolymer; Gantrez AN 119, AN 139, S-97), polyvinyl alcohol, polyacrylic acid, Poloxamer 407 (Pluronic, poly(ethylene oxide)-poly(propylene oxide)-poly (ethylene oxide) triblock copolymer), polyethyleneoxide (Polyox), polyvinyl pyrrolidone-vinyl acetate copolymer (PVP/VA copolymer; Luviskol VA, Plasdone S PVP/VA), polyvinyl pyrrolidone (PVP; K-15~K-120), polyquaternium-11 (Gafquat 755N), polyquaternium-39 (Merquat plus 3330), carboxypolymethylene (Carbomer, Carbopol), hydroxypropyl methyl cellulose, hydroxyethyl cellulose, hydroxypropyl cellulose, gelatin, sodium alginate and the like, and preferably, it may be hydroxypropyl methyl cellulose, polyvinyl pyrrolidone or a mixture thereof.

According to one embodiment of the present invention, mixing ratio of the polymer having solubility parameter ($\delta 1$) of 5 $(MPa)^{1/2}$ to 22 $(MPa)^{1/2}$ and the polymer having solubility parameter ($\delta 2$) of 23.5 $(MPa)^{1/2}$ to 40 $(MPa)^{1/2}$, included in the backing layer (weight ratio of polymer having solubility parameter ($\delta 1$) of 5 $(MPa)^{1/2}$ to 22 $(MPa)^{1/2}$: polymer having solubility parameter ($\delta 2$) of 23.5 $(MPa)^{1/2}$ to 40 $(MPa)^{1/2}$, included in the backing layer) may be 1:0.2 to 4.0, and preferably, it may be 1:0.5 to 2.0. If the weight ratio of the polymer having solubility parameter ($\delta 2$) of 23.5 $(MPa)^{1/2}$ to 40 $(MPa)^{1/2}$ is less than the above range, excessive pressure of force should be applied to degrade the polymer having solubility parameter ($\delta 1$) of 5 $(MPa)^{1/2}$ to 22 $(MPa)^{1/2}$ by tooth brushing, and even if the polymer is degraded, foreign body sensation may be relatively large due to large particle size. If the parameter is over the above range, a drug contained in a drug layer may be transferred to a backing layer and absorbed, thereby causing the backing layer to fail to function properly, and even during use of the patch, the structure is collapsed due to excessively absorbed saliva, thereby causing the backing layer to fail to function properly.

The tooth-attachable patch of the prevent invention can be easily removed by brushing alone after use.

The patch 1 according to one embodiment of the present invention comprises a drug layer 10 in contact with teeth or a surrounding tissue of teeth and a backing layer 20 positioned on one side of the drug layer 10, and in one side of the backing layer 20, a breakable portion 30 is formed.

The breakable portion 30 means a portion processed and treated such that the backing layer 20 can be degraded into a predetermined size by an external force. If the backing layer 20 is broken, the shape of the breakable portion 30 is not particularly limited. For example, the breakable portion 30 may include any shape that the breakable portion 30 is thinner than other portions of the backing layer 20, and the backing layer 20 is allowed to be easily broken along this portion. Preferably, it may include a shape such as prominence and depression 31. In another embodiment, the breakable portion 30 may be formed with a bubble 32 so that the backing layer 20 is allowed to be easily broken.

The breakable portion 30 means a portion that is thinner than other portions of the backing layer 20 but has a certain thickness, and can be distinguished from a pit or a hole formed in the backing layer. Namely, the structure in which a pit or a hole is formed in the backing layer of the patch and the drug component of the drug layer 10 is moved through the hole of the backing layer is not included in the structure of the "breakable portion" of the present invention.

In the case that a pit or a hole is formed in the backing layer and the component of the drug layer 10 is moved through the pit or the hole of the backing layer, the amount of the drug released through the backing layer may increase resulting in loss of the drug to be delivered to teeth or a surrounding tissue of teeth. In the aspect to achieve the original purpose of the backing layer 20, the breakable portion preferably has a structure in which the drug of the drug layer 10 cannot be moved across the backing layer.

According to one embodiment of the present invention, the breakable portion 30 may include a bubble 32. The bubble 32 may have a concave portion 311 in a depth of more than 0 μm and 30 μm or less based on a convex portion.

Pieces degraded through the breakable portion 30 may preferably have the size of about 1 mm in length and width.

The term "break" used herein means that the backing layer is separated into two or more parts, and the patch of the present invention can be easily broken along the breakable portion 30 formed in the backing layer 20. Herein, the meaning that the backing layer 20 is broken is used as a concept including that the backing layer 20 is degraded into a plurality of pieces.

Advantageous Effects

The tooth-attachable patch of the present invention is an easy-to-use type tooth-attachable patch that selectively releases a drug to the surface of teeth without striping off the backing layer.

The patch of the present invention can be degraded and removed by only light tooth brushing.

The patch of the present invention may include various drugs depending on its purpose.

The patch of the present invention have little foreign body sensation because it can make the particle size of the patch remained in the mouth after tooth brushing smaller, and also can provide excellent use sensation.

DESCRIPTION OF DRAWINGS

Other objects and aspects of the present invention will become apparent from the following descriptions of the embodiments with reference to the accompanying drawings in which.

The accompanying drawings illustrate a preferred embodiment of the present invention and together with the foregoing disclosure, serve to provide further understanding of the technical spirit of the present invention, and thus, the present invention is not construed as being limited to the drawing.

BEST MODE

Figure 1:
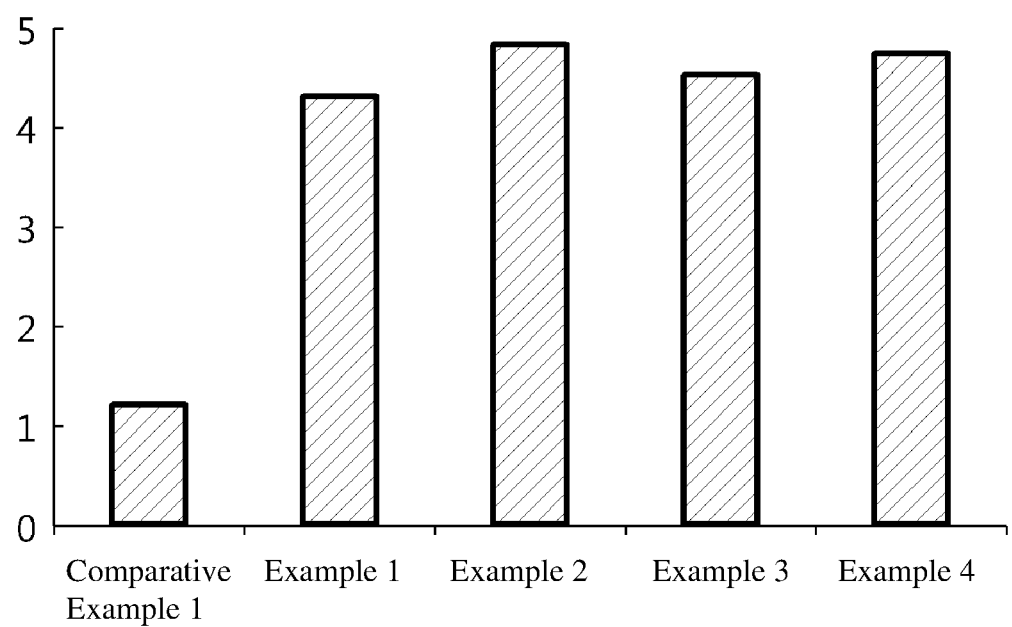
FIG. 1 is a graph showing survey response score as the result of evaluating removability of the patches of Comparative Example 1 and Examples 1 to 4 of the present invention.
Figure 2:
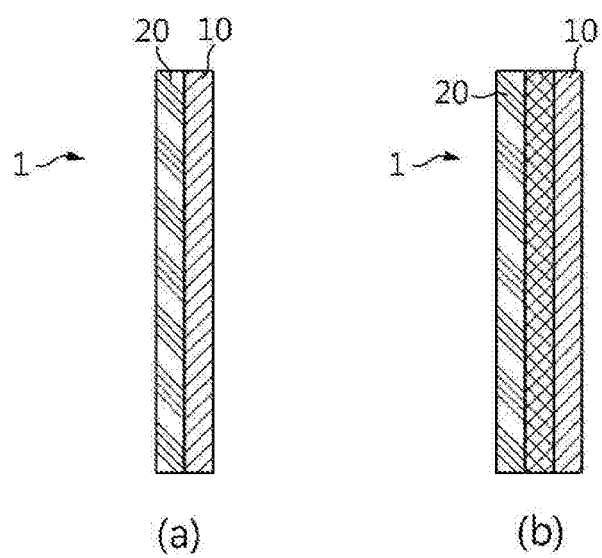
FIG. 2 is a drawing prefiguratively showing the tooth-attachable patch 1 of the present invention. As prefiguratively shown in FIG. 2*a*, the patch may include a drug layer 10 and a backing layer 20, and as shown in FIG. 2*b*, the patch may include another layer separately between the drug layer 10 and the backing layer 20 depending on its purpose.

Hereinafter, preferred embodiments of the present invention will be described in detail with reference to the accompanying drawings. Prior to the description, it should be understood that the terms used in the specification and the appended claims should not be construed as limited to general and dictionary meanings, but interpreted based on the meanings and concepts corresponding to technical aspects of the present invention on the basis of the principle that the inventor is allowed to define terms appropriately for the best explanation. Therefore, the description proposed herein is just a preferable example for the purpose of illustrations only, not intended to limit the scope of the disclosure, so it should be understood that other equivalents and modifications could be made thereto without departing from the scope of the disclosure.

MODE FOR DISCLOSURE

Preparative Example 1

<Preparation of Patch for Tooth Whitening>

Patches for tooth whitening of Comparative Examples having composition of the following Table 1 and Patches for tooth whitening of Examples having composition of the following Table 2 were prepared. % refers to wt %.

TABLE 1

|  |  | Comparative Example 1 |  | Comparative Example 2 |  |
|---|---|---|---|---|---|
| Drug layer | Hydrogen peroxide | 2.9% | Hydrogen peroxide | 2.9% |
|  | Povidone | 19.0% | Povidone | 19.0% |
|  | Glycerin | 3.0% | Glycerin | 3.0% |
|  | Pullulan | 1.0% | Pullulan | 1.0% |
|  | SPAN80 | 5.0% | SPAN80 | 5.0% |
|  | Water etc. | to 100% | Water etc. | to 100% |
| Backing layer | Ethyl Cellulose | 15.0% | Povidone | 15.0% |
|  | Castor oil | 10.0% | glycerin | 3.0% |
|  | Ethanol etc. | to 100% | Pullulan | 1.0% |
|  |  |  | Water etc. | to 100% |

TABLE 2

|  |  | Example 1 |  | Example 2 |  | Example 3 |  | Example 4 |  |
|---|---|---|---|---|---|---|---|---|---|
| Drug layer | Hydrogen peroxide | 2.9% | Hydrogen peroxide | 2.9% | Hydrogen peroxide | 2.9% | Hydrogen peroxide | 2.9% |
|  | Povidone | 19.0% | Povidone | 19.0% | Povidone | 19.0% | Povidone | 19.0% |
|  | Glycerin | 3.0% | Glycerin | 3.0% | Glycerin | 3.0% | Glycerin | 3.0% |
|  | Pullulan | 1.0% | Pullulan | 1.0% | Pullulan | 1.0% | Pullulan | 1.0% |
|  | SPAN80 | 5.0% | SPAN80 | 5.0% | SPAN80 | 5.0% | SPAN80 | 5.0% |
|  | Water etc. | to 100% | Water etc. | to 100% | Water etc. | to 100% | Water etc. | to 100% |
| Backing layer | Ethyl Cellulose | 12.0% | Ethyl Cellulose | 3.0% | Ethyl Cellulose | 12.0% | Ethyl Cellulose | 3.0% |
|  | Hydroxypropyl methylcellulose | 3.0% | Hydroxypropyl methylcellulose | 12.0% | Povidone | 3.0% | Povidone | 12.0% |
|  | Castor oil | 15.0% | Castor oil | 5.0% | Castor oil | 15.0% | Castor oil | 5.0% |
|  | SPAN80 | 5.0% | SPAN80 | 15.0% | SPAN80 | 5.0% | SPAN80 | 15.0% |
|  | Ethanol etc. | to 100% | Ethanol etc. | to 100% | Ethanol etc. | to 100% | Ethanol etc. | to 100% |

Comparative Example 1 of Table 1 is composition for manufacturing a tooth-attachable whitening patch which includes a common water-insoluble supporting material in a backing layer but does not include a water-soluble polymer, and Comparative Example 2 is composition for manufacturing a tooth-attachable whitening patch which only includes a water-soluble polymer in a backing layer.

Patches for tooth whitening having composition of Table 1 and Table 2 were prepared according to the method for preparing a backing layer and a drug reservoir layer in Preparative Example 1 of Korean Patent No. 10-0816250.

<Release Test>

A) Manipulation 0.9% Sodium chloride solution 500 mL is poured in a test tube and a temperature of a test solution is maintained at 32±0.5° C. during drug release test. The tooth whitening patch is fixed on the upper side of a disk which can be used as a sinker without absorbing, interfering or reacting with a double-sided tape so that a tooth attachment surface faces outward. Then, the disk is placed in the test tube with the sample-attached side facing up, and drug release time is calculated from this point of time. The sample-attached disk is aligned parallel to the bottom of the test tube and a paddle blade. Distance between the paddle blade and the sample surface is set to 25±2 mm, and revolutions per minute (rpm) is set to 25. At the time of sampling, 100 mL of sample solution is collected at a fixed position (a position 1 cm away from the wall of the test tube, between the top of the paddle blade and the test liquid surface) 30 min after the start of the test.

B) Amount Measurement a. Reagents

Ammonium molybdate solution

Ammonium molybdate 5.3 g is added to water and adjusted to 50 mL.

Sodium thiosulfate solution

Sodium thiosulfate (pentahydrate) 12.41 g is precisely measured, dissolved in water and adjusted to 1 L to make 0.005 N sodium thiosulfate solution.

b. Method for Measuring Concentration

6 N—HCl 5 mL, potassium iodide about 2 g and 1 drop of ammonium molybdate solution are added to 100 mL of the sample collected from the release test and left in the dark for about 10 min. Starch indicator 3 mL is added thereto and released iodine is titrated with 0.005 N sodium thiosulfate solution.

0.005 N Sodium thiosulfate solution 1 mL=0.08505 mg $H_2O_2$

C) Result

Release rate is calculated by comparing the amount of hydrogen peroxide in the entire product with the amount of hydrogen peroxide calculated through the release test.

TABLE 3

| | Comparative Example 1 | Comparative Example 2 | Example 1 | Example 2 | Example 3 | Example 4 |
|---|---|---|---|---|---|---|
| Release rate (%) | 86.5 | 85.9 | 87.1 | 85.7 | 86.8 | 85.4 |

As can be seen from Table 3, it can be found that the tooth-attachable patches of Examples 1 to 4 have similar hydrogen peroxide release rate to the patch of Comparative Example 1 not containing a water-soluble polymer in a backing layer and the patch of Comparative Example 2 not containing a water-insoluble polymer, respectively.

<Reverse Release Test>

A) Manipulation 0.9% Sodium chloride solution 500 mL is poured in a test tube and a temperature of a test solution is maintained at 32±0.5° C. during drug release test. The tooth whitening patch is fixed on the upper side of a disk which can be used as a sinker without absorbing, interfering or reacting with a double-sided tape so that a tooth attachment surface faces to the disk. Then, the disk is placed in the test tube with the sample-attached side facing up, and drug release time is calculated from this point of time. The sample-attached disk is aligned parallel to the bottom of the test tube and a paddle blade. Distance between the paddle blade and the sample surface is set to 25±2 mm, and revolutions per minute (rpm) is set to 25. At the time of sampling, 100 mL of sample solution is collected at a fixed position (a position 1 cm away from the wall of the test tube, between the top of the paddle blade and the test liquid surface) 30 min after the start of the test.

B) Amount Measurement a. Reagents

Ammonium molybdate solution

Ammonium molybdate 5.3 g is added to water and adjusted to 50 mL.

Sodium thiosulfate solution

Sodium thiosulfate (pentahydrate) 12.41 g is precisely measured, dissolved in water and adjusted to 1 L to make 0.005 N sodium thiosulfate solution.

b. Method for Measuring Concentration

6 N—HCl 5 mL, potassium iodide about 2 g and 1 drop of ammonium molybdate solution are added to 100 mL of the sample collected from the release test and left in the dark for about 10 min. Starch indicator 3 mL is added thereto and released iodine is titrated with 0.005 N sodium thiosulfate solution.

0.005 N Sodium thiosulfate solution 1 mL=0.8505 mg $H_2O_2$

C) Result

Release rate is calculated by comparing the amount of hydrogen peroxide in the entire product with the amount of hydrogen peroxide calculated through the release test.

TABLE 4

| | Comparative Example 1 | Comparative Example 2 | Example 1 | Example 2 | Example 3 | Example 4 |
|---|---|---|---|---|---|---|
| Reverse release rate (%) | 3.2 | 82.8 | 3.3 | 3.8 | 3.5 | 3.7 |

Table 4 shows the reverse release rate of the drug after attaching the sample to the opposite side of the tooth attachment surface, and it is the result of confirming the amount of hydrogen peroxide released through a backing layer.

As can be seen from Table 4, it can be found that in the case of the patch of Comparative Example 1 not containing a water-soluble polymer in a backing layer, the ingredient for whitening teeth contained in a drug layer was not released through the backing layer, but in the case of Comparative Example 2, the drug in a drug layer was released through the backing layer.

Further, it was confirmed that the patches of Examples 1 to 4 have similar reverse release rate to the patch of Comparative Example 1. Through this result, it can be found that the patches of Examples 1 to 4 are well suited to serve as a backing layer of a tooth-attachable patch.

<Survey for Removability>

Survey for removal convenience was conducted to the patches of Comparative Example 1 and Examples 1 to 4 which need a removal process after use, except the patch of Comparative Example 2 which melts away during use. Each of the patches of Comparative Example 1 and Examples 1 to 4 was attached to 30 responders for 15 min according to the group, and then the patch of Comparative Example 1 or Examples 1 to 4 was removed by tooth brushing. Then, each group changed the products and then responded to a questionnaire for removal convenience.

—Criteria for Survey Response—

5: Removal is very convenient and there is no residue on teeth.

4: Removal is convenient but there is little residue.

3: Removal is inconvenient and there is inconvenience due to residue.

2: Removal is inconvenient and there are many residues.

1: Removal is very inconvenient and there are so many residues.

As can be seen from FIG. 1, it can be found that the possibility of a role as a backing layer is similar between those of Comparative Example 1 and Examples 1 to 4, but the patch of Example 1 is difficult to be removed only by tooth brushing.

The patches of Examples 1 to 4 were rated excellent in the removability evaluation, and the users evaluated that the patches generally can be easily removed by tooth brushing after use.

<Evaluation of Tensile Strength>

Evaluation apparatus: ZWICK universal testing machine (Zwick, DE/1494)

Evaluation method: Patches of Comparative Examples 1 and 2 and Examples 1 to 4 were cut into 1 cm×7 cm, set in a jig for measuring tensile strength, and tensile strength was measured at a rate of 0.1 mm/s. Patches of the same size were set again in the jig and wetted with enough amount of water not to flow through the center. After 1 min, tensile strength was measured at a room temperature and 50% relative humidity, and compared with the value measured before moisture contact. Moisture content rate for about 10 sec of the patch wetted with enough moisture was changed little.

As can be seen from Table 5, it was confirmed that Examples 2 and 4 had the highest tensile strength change rate, Examples 1 and 3 had lower tensile strength change rate than Examples 2 and 4, but generally had a higher change rate.

Through this result, it can be found that tensile strength change and removal of the patch attached to teeth were related to each other. In particular, Examples 2 and 4 having high tensile strength change rate showed excellent removability.

<Evaluation of Degradation by Tooth Brushing>

Two sets of Comparative Example 1 and Examples 1 to 4 were prepared. Each patch of one set was shaken in distilled water for 30 min to leave only a backing layer, dried and then weight of the patch was measured. Each patch of the other set was attached to a slide glass, stored in 37° C., 85% humidity environment for 30 min, and then brushed for 3 min using a brushing machine at a rate of 90 times per min back and forth at a load of 250 g. Then, the slide glass, the brushing chamber and the toothbrush were separated, and washed with distilled water while collecting the washing solution. The collected washing solution was filtered through a 1 mm-mesh sieve, and residue was dried and weighed to check a ratio of the residue based on the total weight of the backing layer.

As a result, it was confirmed that the patch of Comparative Example 1 has a residue ratio of 98% or more, but in the case of the patches of Examples 1 to 4, in which tensile strength was increased by 50% or more compared to before moisture absorption, dry weight of the residue obtained after filtering through a 1 mm-mesh sieve was less than 5%. It was confirmed that the present invention having excellent tensile strength change rate can be easily degraded and removed by tooth brushing.

Preparative Example 2

<Preparation of Patch for Tooth Whitening>

Patches for tooth whitening of Comparative Examples 3 and 4 having composition of the following Table 6 and patches for tooth whitening of Examples 5 to 8 having composition of the following Table 7 were prepared.

TABLE 5

| | Comparative Example 1 | Comparative Example 2 | Example 1 | Example 2 | Example 3 | Example 4 |
|---|---|---|---|---|---|---|
| Tensile strength change rate (%) | −0.8 | Unable to measure | −65.6 | −91.3 | −67.9 | −93.3 |

(−): Indicated by - because tensile strength is reduced compared to before water absorption.

TABLE 6

| | | Comparative Example 3 | | Comparative Example 4 | |
|---|---|---|---|---|---|
| Drug layer | Hydrogen peroxide | 2.9% | Hydrogen peroxide | 2.9% | |
| | Povidone | 19.0% | Povidone | 19.0% | |
| | Glycerin | 3.0% | Glycerin | 3.0% | |
| | Pullulan | 1.0% | Pullulan | 1.0% | |
| | SPAN80 | 5.0% | SPAN80 | 5.0% | |
| | Water etc. | to 100% | Water etc. | to 100% | |
| Backing layer | Ethyl Cellulose | 15.0% | Povidone | 15.0% | |
| | Castor oil | 10.0% | glycerin | 3.0% | |
| | Ethanol etc. | to 100% | Pullulan | 1.0% | |
| | | | Water etc. | to 100% | |

TABLE 7

| | | Example 5 | | Example 6 | | Example 7 | | Example 8 | |
|---|---|---|---|---|---|---|---|---|---|
| Drug layer | Hydrogen peroxide | 2.9% | Hydrogen peroxide | 2.9% | Hydrogen peroxide | 2.9% | Hydrogen peroxide | 2.9% | |
| | Povidone | 19.0% | Povidone | 19.0% | Povidone | 19.0% | Povidone | 19.0% | |
| | Glycerin | 3.0% | Glycerin | 3.0% | Glycerin | 3.0% | Glycerin | 3.0% | |
| | Pullulan | 1.0% | Pullulan | 1.0% | Pullulan | 1.0% | Pullulan | 1.0% | |

TABLE 7-continued

|  | Example 5 |  | Example 6 |  | Example 7 |  | Example 8 |  |
|---|---|---|---|---|---|---|---|---|
| | SPAN80 | 5.0% | SPAN80 | 5.0% | SPAN80 | 5.0% | SPAN80 | 5.0% |
| | Water etc. | to 100% | Water etc. | to 100% | Water etc. | to 100% | Water etc. | to 100% |
| Backing layer | Ethyl Cellulose | 12.0% | Ethyl Cellulose | 3.0% | Ethyl Cellulose | 12.0% | Ethyl Cellulose | 3.0% |
| | Hydroxypropyl methylcellulose | 3.0% | Hydroxypropyl methylcellulose | 12.0% | Povidone | 3.0% | Povidone | 12.0% |
| | Castor oil | 15.0% | Castor oil | 5.0% | Castor oil | 15.0% | Castor oil | 5.0% |
| | SPAN80 | 5.0% | SPAN80 | 15.0% | SPAN80 | 5.0% | SPAN80 | 15.0% |
| | Ethanol etc. | to 100% | Ethanol etc. | to 100% | Ethanol etc. | to 100% | Ethanol etc. | to 100% |

Patches for tooth whitening having composition of Table 6 and Table 7 were prepared according to the method for preparing a backing layer and a drug reservoir layer in Preparative Example 1 of Korean Patent No. 10-0816250.

<Release Test>

A) Manipulation 0.9% Sodium chloride solution 500 mL is poured in a test tube and a temperature of a test solution is maintained at 32±0.5° C. during drug release test. The tooth whitening patch is fixed on the upper side of a disk which can be used as a sinker without absorbing, interfering or reacting with a double-sided tape so that a tooth attachment surface faces outward. Then, the disk is placed in the test tube with the sample-attached side facing up, and drug release time is calculated from this point of time. The sample-attached disk is aligned parallel to the bottom of the test tube and a paddle blade. Distance between the paddle blade and the sample surface is set to 25±2 mm, and revolutions per minute (rpm) is set to 25. At the time of sampling, 100 mL of sample solution is collected at a fixed position (a position 1 cm away from the wall of the test tube, between the top of the paddle blade and the test liquid surface) 30 min after the start of the test.

B) Amount Measurement a. Reagents

Ammonium molybdate solution

Ammonium molybdate 5.3 g is added to water and adjusted to 50 mL.

Sodium thiosulfate solution

Sodium thiosulfate (pentahydrate) 12.41 g is precisely measured, dissolved in water and adjusted to 1 L to make 0.005 N sodium thiosulfate solution.

b. Method for Measuring Concentration

6 N—HCl 5 mL, potassium iodide about 2 g and 1 drop of ammonium molybdate solution are added to 100 mL of the sample collected from the release test and left in the dark for about 10 min. Starch indicator 3 mL is added thereto and released iodine is titrated with 0.005 N sodium thiosulfate solution.

0.005 N Sodium thiosulfate solution 1 mL=0.8505 mg $H_2O_2$

Release rate is calculated by comparing the amount of hydrogen peroxide in the entire product with the amount of hydrogen peroxide calculated through the release test.

TABLE 8

|  | Comparative Example 3 | Comparative Example 4 | Example 5 | Example 6 | Example 7 | Example 8 |
|---|---|---|---|---|---|---|
| Release rate (%) | 85.5 | 84.8 | 86.1 | 85.1 | 85.6 | 85.7 |

As can be seen from Table 8, it can be found that all tooth-attachable patches of Comparative Examples and Examples show similar hydrogen peroxide release rate. Namely, it can be found that release efficiency of the ingredient for whitening teeth of the patch of the present invention has excellent release rate similar to the patch having water-insoluble backing layer and the patch having soluble backing layer.

<Reverse Release Test>

A) Manipulation 0.9% Sodium chloride solution 500 mL is poured in a test tube and a temperature of a test solution is maintained at 32±0.5° C. during drug release test. The tooth whitening patch is fixed on the upper side of a disk which can be used as a sinker without absorbing, interfering or reacting with a double-sided tape so that a tooth attachment surface faces to the disk. Then, the disk is placed in the test tube with the sample-attached side facing up, and drug release time is calculated from this point of time. The sample-attached disk is aligned parallel to the bottom of the test tube and a paddle blade. Distance between the paddle blade and the sample surface is set to 25±2 mm, and revolutions per minute (rpm) is set to 25. At the time of sampling, 100 mL of sample solution is collected at a fixed position (a position 1 cm away from the wall of the test tube, between the top of the paddle blade and the test liquid surface) 30 min after the start of the test.

B) Amount Measurement a. Reagents

Ammonium molybdate solution

Ammonium molybdate 5.3 g is added to water and adjusted to 50 mL.

Sodium thiosulfate solution

Sodium thiosulfate (pentahydrate) 12.41 g is precisely measured, dissolved in water and adjusted to 1 L to make 0.005 N sodium thiosulfate solution.

b. Method for Measuring Concentration

6 N—HCl 5 mL, potassium iodide about 2 g and 1 drop of ammonium molybdate solution are added to 100 mL of the sample collected from the release test and left in the dark for about 10 min. Starch indicator 3 mL is added thereto and released iodine is titrated with 0.005 N sodium thiosulfate solution.

0.005 N Sodium thiosulfate solution 1 mL=0.8505 mg $H_2O_2$

Release rate is calculated by comparing the amount of hydrogen peroxide in the entire product with the amount of hydrogen peroxide calculated through the release test.

TABLE 9

| | Comparative Example 3 | Comparative Example 4 | Example 5 | Example 6 | Example 7 | Example 8 |
|---|---|---|---|---|---|---|
| Reverse release rate (%) | 3.5 | 80.8 | 3.7 | 3.9 | 3.1 | 4.0 |

The patch of Comparative Example 4 of Table 9 is a patch including a water-soluble polymer in a backing layer. The patch of Comparative Example 4 shows that the hydrogen peroxide contained in a drug layer can be released through a backing layer rather than only delivered to the target site. It can be found that the patches of Comparative Example 3 and Examples 5 to 8 have very low reverse release rate. This shows that the water-insoluble polymer used in the backing layer can block hydrogen peroxide from permeating through the backing layer.

<Survey for Removability>

Survey for removal convenience was conducted to patches of Comparative Example 3 and Examples 5 to 8 which need a removal process after use, except a patch of Comparative Example 4 which melts away during use. Each of the patches of Comparative Example 3 and Examples 5 to 8 was attached to 30 responders for 15 min according to the group, and then the patch of Comparative Example 3 or Examples 5 to 8 was removed by tooth brushing. Then, each group changed the products and then responded to a questionnaire for removal convenience.

—Criteria for Survey Response—

5: Removal is very convenient and there is no residue on teeth.
4: Removal is convenient but there is little residue.
3: Removal is inconvenient and there is inconvenience due to residue.
2: Removal is inconvenient and there are many residues.
1: Removal is very inconvenient and there are so many residues.

Figure 3:
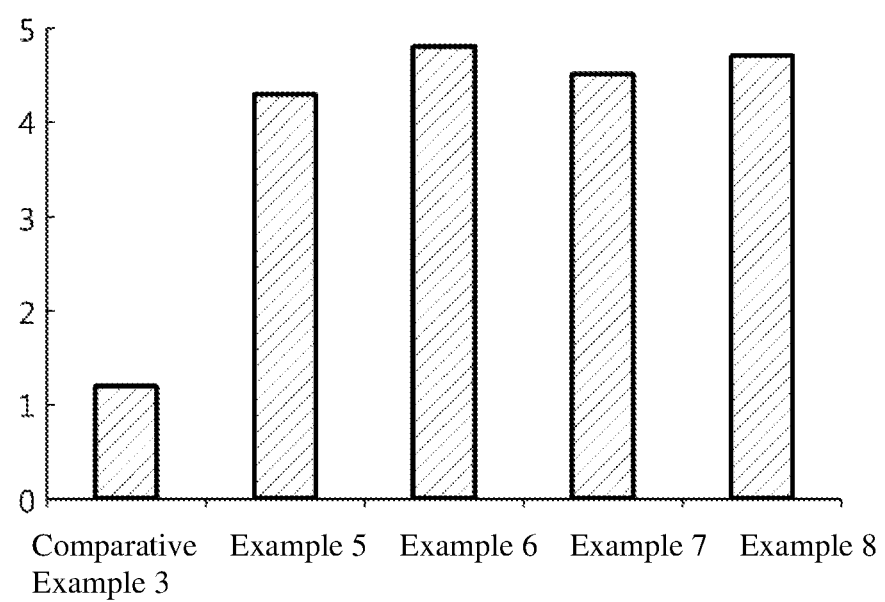
FIG. 3 is a graph showing the result of evaluating removability of the patches of Comparative Example 3 and Examples 5 to 8 of the present invention.

As can be seen from FIG. 3, when the user brushed teeth at 15 min after attaching the patch of Comparative Example 3, it was evaluated that removal was generally inconvenient and there were residues.

However, the patches of Examples 5 to 8 mostly got 4 points or more, and most of them were evaluated that removal was convenient.

It was confirmed that all patches of Comparative Example 3 and Examples 5 to 8 show an excellent effect on controlling reverse release of the hydrogen peroxide contained in a drug layer. However, it was confirmed that unlike the patches of Examples 5 to 8, the patch of Comparative Example 3 is not easily removed by tooth brushing alone after attachment to teeth.

<Evaluation of Contact Angle>

Evaluation apparatus: FM40 Easy Drop (Kruss, Germany)

Evaluation method: Each patch of Comparative Examples 3 and 4 or Examples 5 to 8 was cut into 1 cm×3 cm, put on a testing bench of an apparatus, and then 5 μl of water was dropped thereon. Then contact angle from 10 sec to 300 sec was measured at a room temperature (about 20° C.) under typical laboratory conditions, and variation was calculated.

TABLE 10

| | Comparative Example 3 | Comparative Example 4 | Example 5 | Example 6 | Example 7 | Example 8 |
|---|---|---|---|---|---|---|
| Static contact angle variation (°) | 1.2 | Unable to measure | 15.1 | 40.5 | 17.7 | 43.6 |

As can be seen form Table 10, it can be found that contact angle variation of the patches of Examples 5 to 8 is 10 times or more than that of the patch of Comparative Example 3.

In particular, it was found that the patches of Examples 5 to 8 have excellent removability by tooth brushing, and this is thought to be the influence by the contact angle variation of Table 10.

Preparative Example 3

<Preparation of Patch for Tooth Whitening>

Patches for tooth whitening of Comparative Examples 5 and 6 having composition of the following Table 11 and patches for tooth whitening of Examples 9 to 12 having composition of the following Table 12 were prepared.

TABLE 11

| | Comparative Example 5 | | Comparative Example 6 | |
|---|---|---|---|---|
| Drug layer | Hydrogen peroxide | 2.9% | Hydrogen peroxide | 2.9% |
| | Povidone | 19.0% | Povidone | 19.0% |
| | Glycerin | 3.0% | Glycerin | 3.0% |
| | Pullulan | 1.0% | Pullulan | 1.0% |
| | SPAN80 | 5.0% | SPAN80 | 5.0% |
| | Water etc. | to 100% | Water etc. | to 100% |
| Backing layer | Ethyl Cellulose | 15.0% | Povidone | 15.0% |
| | Castor oil | 10.0% | glycerin | 3.0% |
| | Ethanol etc. | to 100% | Pullulan | 1.0% |
| | | | Water etc. | to 100% |

TABLE 12

| | | Example 9 | | Example 10 | | Example 11 | | Example 12 | |
|---|---|---|---|---|---|---|---|---|---|
| Drug layer | Hydrogen peroxide | | 2.9% | Hydrogen peroxide | 2.9% | Hydrogen peroxide | 2.9% | Hydrogen peroxide | 2.9% |
| | Povidone | | 19.0% | Povidone | 19.0% | Povidone | 19.0% | Povidone | 19.0% |
| | Glycerin | | 3.0% | Glycerin | 3.0% | Glycerin | 3.0% | Glycerin | 3.0% |
| | Pullulan | | 1.0% | Pullulan | 1.0% | Pullulan | 1.0% | Pullulan | 1.0% |
| | SPAN80 | | 5.0% | SPAN80 | 5.0% | SPAN80 | 5.0% | SPAN80 | 5.0% |
| | Water etc. | | to 100% | Water etc. | to 100% | Water etc. | to 100% | Water etc. | to 100% |

TABLE 12-continued

| | Example 9 | | Example 10 | | Example 11 | | Example 12 | |
|---|---|---|---|---|---|---|---|---|
| Backing layer | Ethyl Cellulose | 12.0% | Ethyl Cellulose | 3.0% | Ethyl Cellulose | 12.0% | Ethyl Cellulose | 3.0% |
| | Hydroxypropyl methylcellulose 2910 | 3.0% | Hydroxypropyl methylcellulose 2910 | 12.0% | Povidone | 3.0% | Povidone | 12.0% |
| | Castor oil | 15.0% | Castor oil | 5.0% | Castor oil | 15.0% | Castor oil | 5.0% |
| | SPAN80 | 5.0% | SPAN80 | 15.0% | SPAN80 | 5.0% | SPAN80 | 15.0% |
| | Ethanol etc. | to 100% | Ethanol etc. | to 100% | Ethanol etc. | to 100% | Ethanol etc. | to 100% |

Patches for tooth whitening having composition of Table 11 and Table 12 were prepared according to the method for preparing a backing layer and a drug reservoir layer in Preparative Example 1 of Korean Patent No. 10-0816250.

Solubility parameter of each polymer for forming a backing layer contained in the backing layer of Examples 9 to 12 is as follows.

Ethyl cellulose: 20.6

HPMC (Hydroxypropyl methylcellulose) 2910: 30

PVP (Polyvinylpyrrolidone): 24.9

<Release Test>

A) Manipulation 0.9% Sodium chloride solution 500 mL is poured in a test tube and a temperature of a test solution is maintained at 32±0.5° C. during drug release test. The tooth whitening patch is fixed on the upper side of a disk which can be used as a sinker without absorbing, interfering or reacting with a double-sided tape so that a tooth attachment surface faces outward. Then, the disk is placed in the test tube with the sample-attached side facing up, and drug release time is calculated from this point of time. The sample-attached disk is aligned parallel to the bottom of the test tube and a paddle blade. Distance between the paddle blade and the sample surface is set to 25±2 mm, and revolutions per minute (rpm) is set to 25. At the time of sampling, 100 mL of sample solution is collected at a fixed position (a position 1 cm away from the wall of the test tube, between the top of the paddle blade and the test liquid surface) 30 min after the start of the test.

B) Amount Measurement a. Reagents

Ammonium molybdate solution

Ammonium molybdate 5.3 g is added to water and adjusted to 50 mL.

Sodium thiosulfate solution

Sodium thiosulfate (pentahydrate) 12.41 g is precisely measured, dissolved in water and adjusted to 1 L to make 0.005 N sodium thiosulfate solution.

b. Method for Measuring Concentration

6 N—HCl 5 mL, potassium iodide about 2 g and 1 drop of ammonium molybdate solution are added to 100 mL of the sample collected from the release test and left in the dark for about 10 min. Starch indicator 3 mL is added thereto and released iodine is titrated with 0.005 N sodium thiosulfate solution.

0.005 N Sodium thiosulfate solution 1 mL=0.8505 mg $H_2O_2$

C) Result

Release rate is calculated by comparing the amount of hydrogen peroxide in the entire product with the amount of hydrogen peroxide calculated through the release test, and shown in the following Table 13.

TABLE 13

| | Comparative Example 5 | Comparative Example 6 | Example 9 | Example 10 | Example 11 | Example 12 |
|---|---|---|---|---|---|---|
| Release rate (wt %) | 85.9 | 89.7 | 86.4 | 84.9 | 86.8 | 84.6 |

As can be seen from Table 13, it can be found that all tooth-attachable patches of Comparative Examples and Examples show similar hydrogen peroxide release rate. Namely, it can be found that release efficiency of the ingredient for whitening teeth of the patch of the present invention has excellent release rate similar to the patch having water-insoluble backing layer and the patch having soluble backing layer.

<Reverse Release Test>

A) Manipulation 0.9% Sodium chloride solution 500 mL is poured in a test tube and a temperature of a test solution is maintained at 32±0.5° C. during drug release test. The tooth whitening patch is fixed on the upper side of a disk which can be used as a sinker without absorbing, interfering or reacting with a double-sided tape so that a tooth attachment surface faces to the disk. Then, the disk is placed in the test tube with the sample-attached side facing up, and drug release time is calculated from this point of time. The sample-attached disk is aligned parallel to the bottom of the test tube and a paddle blade. Distance between the paddle blade and the sample surface is set to 25±2 mm, and revolutions per minute (rpm) is set to 25. At the time of sampling, 100 mL of sample solution is collected at a fixed position (a position 1 cm away from the wall of the test tube, between the top of the paddle blade and the test liquid surface) 30 min after the start of the test.

B) Amount Measurement a. Reagents

Ammonium molybdate solution

Ammonium molybdate 5.3 g is added to water and adjusted to 50 mL.

Sodium thiosulfate solution

Sodium thiosulfate (pentahydrate) 12.41 g is precisely measured, dissolved in water and adjusted to 1 L to make 0.005 N sodium thiosulfate solution.

b. Method for Measuring Concentration

6 N—HCl 5 mL, potassium iodide about 2 g and 1 drop of ammonium molybdate solution are added to 100 mL of the sample collected from the release test and left in the dark for about 10 min. Starch indicator 3 mL is added thereto and released iodine is titrated with 0.005 N sodium thiosulfate solution.

0.005 N Sodium thiosulfate solution 1 mL=0.8505 mg $H_2O_2$

C) Result

Release rate is calculated by comparing the amount of hydrogen peroxide in the entire product with the amount of hydrogen peroxide calculated through the release test, and shown in the following Table 14.

TABLE 14

|  | Comparative Example 5 | Comparative Example 6 | Example 9 | Example 10 | Example 11 | Example 12 |
|---|---|---|---|---|---|---|
| Reverse release rate (%) | 3.7 | 82.7 | 3.3 | 3.5 | 3.1 | 3.8 |

The patch of Comparative Example 6 of Table 14 is a patch including a water-soluble polymer in a backing layer.

The patch of Comparative Example 6 shows that the hydrogen peroxide contained in a drug layer can be reversely released through a backing layer thereby also releasing a drug in the opposite direction to teeth rather than only delivered to the target site. It can be found that the patches of Comparative Example 5 and Examples 9 to 12 have very low reverse release rate. This shows that the water-insoluble polymer used in the backing layer can block hydrogen peroxide from permeating through the backing layer.

<Survey for Removability>

Survey for removal convenience was conducted to patches of Comparative Example 5 and Examples 9 to 12 which need a removal process after use, except a patch of Comparative Example 4 which melts away during use. Each of the patches of Comparative Example 5 and Examples 9 to 12 was attached to 30 responders for 15 min according to the group, and then the patch of Comparative Example 5 or Examples 9 to 12 was removed by tooth brushing. Then, each group changed the products and then responded to a questionnaire for removal convenience.

—Criteria for Survey Response—

5: Removal is very convenient and there is no residue on teeth.

4: Removal is convenient but there is little residue.

3: Removal is inconvenient and there is inconvenience due to residue.

2: Removal is inconvenient and there are many residues.

1: Removal is very inconvenient and there are so many residues.

Figure 4:
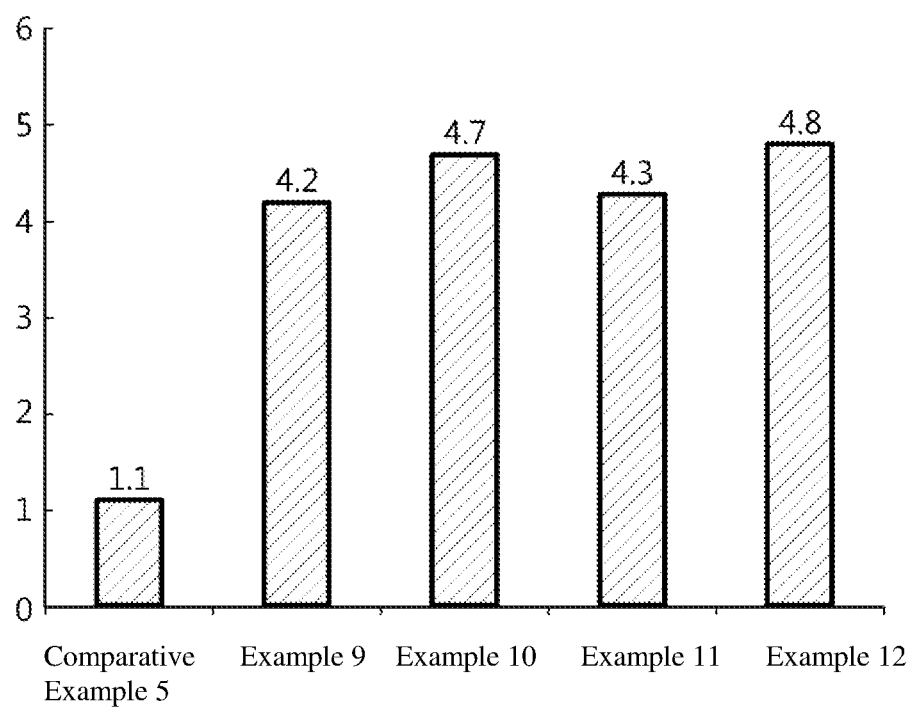
FIG. 4 is a graph showing the result of evaluating removability of the patches of Comparative Example 5 and Examples 9 to 12 of the present invention.

As can be seen from FIG. 4, when the user brushed teeth at 15 min after attaching the patch of Comparative Example 5, it was evaluated that removal was generally inconvenient and there were residues.

However, the patches of Examples 9 to 12 mostly got 4 points or more, and most of them were evaluated that removal was convenient.

It was confirmed that all patches of Comparative Example 5 and Examples 9 to 12 show an excellent effect on controlling reverse release of the hydrogen peroxide contained in a drug layer. However, it was confirmed that unlike the patches of Examples 9 to 12, the patch of Comparative Example 5 is not easily removed by tooth brushing alone after attachment to teeth.

Preparative Example 4

<Preparation of Patch for Tooth Whitening>

Patches for tooth whitening having composition of the following Table 15 were prepared.

TABLE 15

|  |  | Comparative Example 7 |  | Example 13 |  | Example 14 |  |
|---|---|---|---|---|---|---|---|
| Breakable portion |  | No |  | Bubble |  | Prominence and depression |  |
| Drug layer | Hydrogen peroxide | 2.9% | Hydrogen peroxide | 2.9% | Hydrogen peroxide | 2.9% |  |
|  | Povidone | 19.0% | Povidone | 19.0% | Povidone | 19.0% |  |
|  | Glycerin | 3.0% | Glycerin | 3.0% | Glycerin | 3.0% |  |
|  | Pullulan | 1.0% | Pullulan | 1.0% | Pullulan | 1.0% |  |
|  | Water etc. | to 100% | Water etc. | to 100% | Water etc. | to 100% |  |
| Backing layer | Ethyl Cellulose | 20.0% | Ethyl Cellulose | 20.0% | Ethyl Cellulose | 20.0% |  |
|  | Castor oil | 10.0% | Castor oil | 10.0% | Castor oil | 10.0% |  |
|  | Ethanol etc. | to 100% | Ethanol etc. | to 100% | Ethanol etc. | to 100% |  |

After preparing a patch according to a prescription of the above Table, for Examples, bubbles (Example 13), and prominence and depression (Example 14) were formed on the backing layer or the entire patch.

The prominence and depression was formed by pressing the patch using a grid, and bubbles are artificially formed by using a homo-mixer and the like just prior to application of the backing layer.

The lines constituting the grid have width of 0.1 mm or less and its depth is varied according to the thickness of the patch. After the prominence and depression is formed, the thickness of the concave portion of the patch should be 30 μm or less and the interval between grids should be 1 mm.

Patches for tooth whitening having composition of the Table 15 were prepared according to the method for preparing a backing layer and a drug reservoir layer in Preparative Example 1 of Korean Patent No. 10-0816250.

<Survey for Removal Convenience>

For each group of 30 individuals, 5 groups used in patches of Comparative Example 7 and Examples 13 and 14. Two groups using Comparative Example 7 stripped off the patches after 30 min attachment or removed the patches by tooth brushing. The groups using the patches of Examples 13 and 14 removed the patches by tooth brushing after 30 min attachment. Then, survey for removal convenience was conducted for each group.

—Criteria for Survey Response—

5: Removal is very convenient and there is no residue.

4: Removal is convenient but there is little residue.

3: Removal is inconvenient and there is inconvenience due to residue.

2: Removal is inconvenient and there are many residues.

1: Removal is very inconvenient and there are so many residues.

Figure 5:
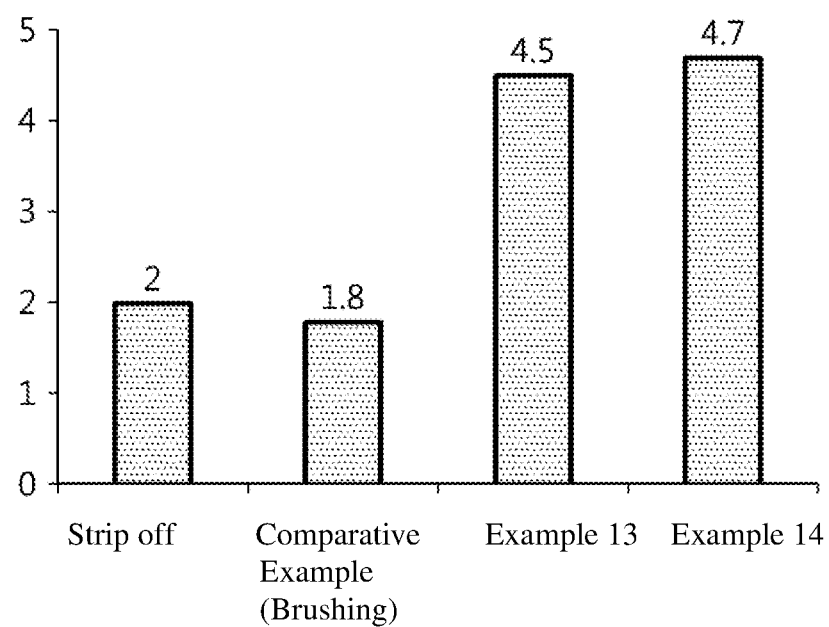
FIG. 5 is a graph showing the result of evaluating removability of the patches of Comparative Example 7 and Examples 13 and 14.
Figure 6:
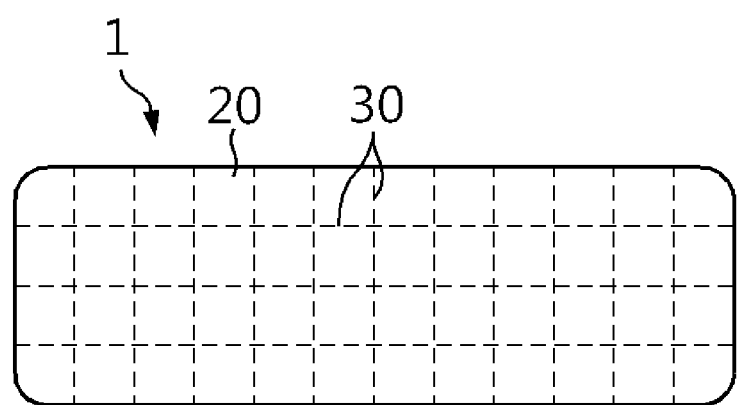
FIG. 6 is a drawing prefiguratively showing an example of the patch 1 including the breakable portion 30 of the present invention.
Figure 7:
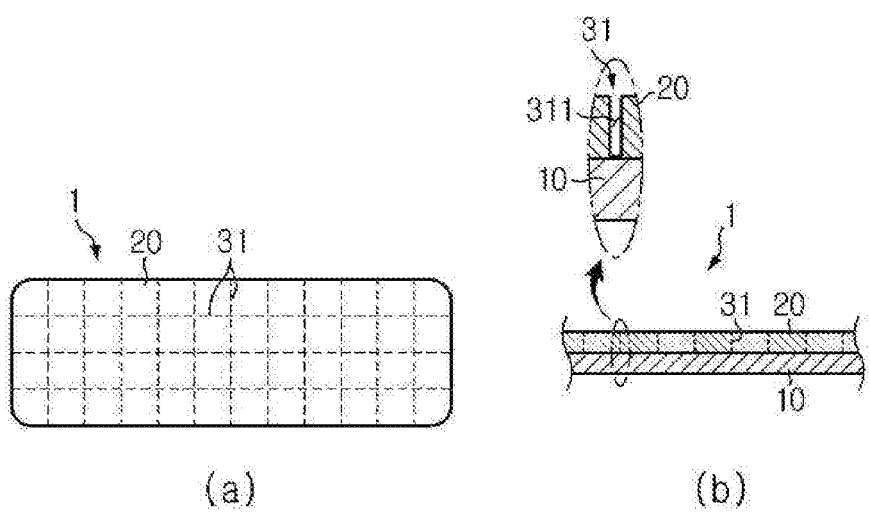
FIG. 7 is a drawing prefiguratively showing an example that the breakable portion 30 includes prominence and depression 31 in the patch 1 including the breakable portion 30 of the present invention.
Figure 8:
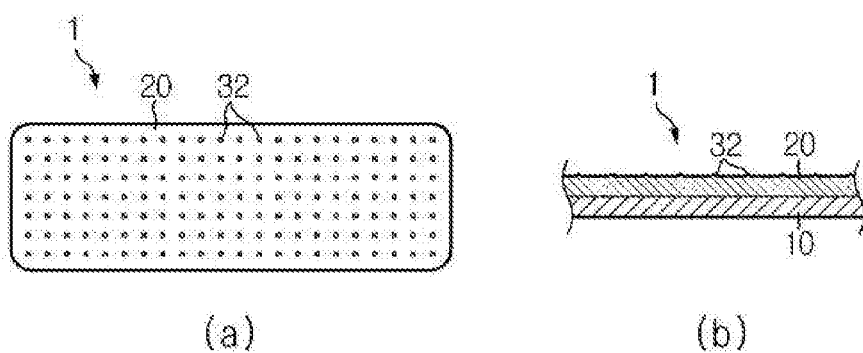
FIG. 8 is a drawing prefiguratively showing an example that the breakable portion 30 includes a bubble 32 in the patch 1 including the breakable portion 30 of the present invention.

As can be seen from FIG. 5, when the user brushed teeth at 30 min after attaching the patch of Comparative Example 7, it was evaluated that removal was generally inconvenient and there were many residues.

However, the patches of Examples 13 and 14 mostly got 4 points or higher, and most of them were evaluated that removal was convenient.

<Evaluation of Degradation by Tooth Brushing>

Two sets of Comparative Example 7 and Examples 13 and 14 were prepared to the same size. Each patch of one set was shaken in distilled water for 30 min to leave only a backing layer, dried and then weight of the patch was measured. Each patch of the other set was attached to a slide glass, stored in 37° C., 85% humidity environment for 30 min, and then brushed for 3 min using a brushing machine at a rate of 90 times per min back and forth at a load of 250 g. Then, the slide glass, the brushing chamber and the toothbrush were separated, and washed with distilled water while collecting the washing solution. The collected washing solution was filtered through a 1 mm-mesh sieve, and residue was dried and weighed to calculate a ratio of the residue based on the total weight of the backing layer.

TABLE 16

|  | Comparative Example 7 | Example 13 | Example 14 |
|---|---|---|---|
| Residue ratio (wt %) | 96.8 | 1.3 | 1.5 |

As can be seen from Table 16, it was confirmed that the patch of Comparative Example 7 was hardly degraded by tooth brushing, and could not pass through the 1 mm-mesh sieve. Namely, about 96 wt % or more of the patch was remained on the sieve.

However, the patches of Examples 13 and 14 were remained about 1.3 wt %, 1.5 wt % of dry weight based on initial weight, respectively.

As can be seen from the result, it was confirmed that the patches were easily degraded by the breakable portion form on the patches of Examples 13 and 14, and it was conveniently removed by tooth brushing.

INDUSTRIAL APPLICABILITY

The present invention can provide a patch which can be easily removed by tooth brushing after being attached to teeth or a surrounding part of teeth.

The present invention has been described in detail. However, it should be understood that the detailed description and specific examples, while indicating preferred embodiments of the disclosure, are given by way of illustration only, since various changes and modifications within the scope of the disclosure will become apparent to those skilled in the art from this detailed description.

What is claimed is:

1. A patch for attaching to teeth or a surrounding part of teeth, which comprises:
    a drug layer including a drug component; and
    a backing layer which is positioned on one side of the drug layer,
    wherein the backing layer includes a water-soluble polymer and water-insoluble polymer,
    wherein the water-insoluble polymer is at least one selected from the group consisting of cellulose acetate phthalate, shellac, polyvinyl acetate, ethyl cellulose, polymethyl methacrylate, methacryloyl ethyl betaine/methacrylate copolymer, methacrylic acid copolymer and aminoalkyl methacrylate copolymer, and
    the water-soluble polymer is at least one selected from the group consisting of polyalkyl vinyl ether-maleic acid copolymer (PVM/MA copolymer), polyvinyl alcohol, polyacrylic acid, Poloxamer 407, polyethyleneoxide (Polyox), polyvinyl pyrrolidone-vinyl acetate copolymer (PVP/VA copolymer), polyvinyl pyrrolidone (PVP), polyquaternium-11, polyquaternium-39, carboxypolymethylene (Carbomer), hydroxypropyl methyl cellulose, hydroxyethyl cellulose, hydroxypropyl cellulose, gelatin and sodium alginate,
    wherein a tensile strength of the backing layer is reduced by 50% or more upon moisture absorption, compared to a tensile strength before moisture absorption, and
    wherein the backing layer is capable of being degraded, dispersed into particles and detached by tooth brushing.

2. The patch of claim 1, wherein the tensile strength of the backing layer of the patch, which is measured in a state that moisture is sufficiently absorbed so that the moisture content rate does not change for 10 sec, and measured at an environment of temperature of 25° C. using Zwick, DE/1494 universal testing machine at a rate of 0.1 mm/s, is reduced by 50% or more, compared to before moisture absorption.

3. The patch of claim 1, wherein the backing layer has tensile strength reduction rate of 60% to 95%, compared to before moisture absorption.

4. The patch of claim 1, wherein a weight ratio of the water-soluble polymer and the water-insoluble polymer included in the backing layer (water-soluble polymer : water-insoluble polymer) is 1:4 to 4:1.

5. The patch of claim 1, wherein the water-insoluble polymer is ethyl cellulose.

6. The patch of claim 1, wherein the drug layer comprises at least one selected from the group consisting of an ingredient for whitening teeth, an ingredient for preventing or improving sensitive teeth, an ingredient for preventing cavities, and an ingredient for preventing periodontal disease.

7. The patch of claim 6,
    wherein the ingredient for whitening teeth is:
    at least one peroxide selected from the group consisting of hydrogen peroxide, carbamide peroxide, calcium peroxide, sodium percarbonate, sodium perborate, tetrasodium pyrophosphate peroxidate and a mixture thereof;
    at least one polyphosphate selected from the group consisting of tetrasodium pyrophosphate (TSPP), sodium acid pyrophosphate (SAPP), sodium hexametaphosphate (SHMP), sodium tripolyphosphate (STP), sodium potassium tripolyphosphate (SKTP), tetrapotassium pyrophosphate (TKPP), ultra-metaphosphate as ultra-phosphate, acidic sodium polyphosphate and a mixture thereof;
    wherein the ingredient for preventing or improving sensitive teeth or cavities is at least one selected from the group consisting of strontium chloride, calcium carbonate, sodium citrate, sodium fluoride, silica, hydroxyapatite, potassium nitrate and potassium phosphate,
    wherein the ingredient for preventing periodontal disease is at least one selected from the group consisting of bamboo salt, titrated Extract of Zea Mays L. unsaponifiable fraction, policresulen, tetracycline, chlorhexidine gluconate, cetyl pyridinium chloride, sanguinarine, triclosan, Magnoliae Cortex, Centella Asiatica, Chamomile, Rhatany, Myrrha, Mori Cortex Radicis, Cimicifugae Rhizoma, Green tea, Glycyrrhizae Radix et Rhizoma, Scutellariae Radix, Taraxaci Herba and Lonicerae Flos.

8. A patch for attaching to teeth or a surrounding part of teeth, which comprises:
a drug layer attached to teeth or a surrounding part of teeth; and
a backing layer which is positioned on one side of the drug layer,
wherein the backing layer includes a water-soluble polymer and water-insoluble polymer,
wherein the water-insoluble polymer is at least one selected from the group consisting of cellulose acetate phthalate, shellac, polyvinyl acetate, ethyl cellulose, polymethyl methacrylate, methacryloyl ethyl betaine/methacrylate copolymer, methacrylic acid copolymer and aminoalkyl methacrylate copolymer, and
the water-soluble polymer is at least one selected from the group consisting of polyalkyl vinyl ether-maleic acid copolymer (PVM/MA copolymer), polyvinyl alcohol, polyacrylic acid, Poloxamer 407, polyethyleneoxide (Polyox), polyvinyl pyrrolidone-vinyl acetate copolymer (PVP/VA copolymer), polyvinyl pyrrolidone (PVP), polyquaternium-11, polyquaternium-39, carboxypolymethylene (Carbomer), hydroxypropyl methyl cellulose, hydroxyethyl cellulose, hydroxypropyl cellulose, gelatin and sodium alginate,
wherein the backing layer has a static contact angle which varies over time,
wherein the backing layer is capable of being degraded by tooth brushing, and dispersed into particles.

9. The patch of claim 8, wherein the static contact angle varies from 13° to 50° over 10 sec to 300 sec when measured at a temperature of 20° C.

10. A patch for attaching to teeth or a surrounding part of teeth, which comprises: a drug layer in contact with teeth or a surrounding part of teeth; and
a backing layer positioned on one side of the drug layer,
wherein the backing layer includes a polymer having solubility parameter ($\delta 1$) of 5 $(MPa)^{1/2}$ to 22 $(MPa)^{1/2}$; and a polymer having solubility parameter ($\delta 2$) of 23.5 $(MPa)^{1/2}$ to 40 $(MPa)^{1/2}$,
wherein the polymer having solubility parameter ($\delta 1$) of 5 $(MPa)^{1/2}$ to 22 $(MPa)^{1/2}$ is any one selected from the group consisting of cellulose acetate phthalate, shellac, polyvinyl acetate, ethyl cellulose, polymethyl methacrylate, methacryloyl ethyl betaine/methacrylate copolymer, methacrylic acid copolymer, aminoalkyl methacrylate copolymer and a mixture thereof, and
wherein the backing layer is capable of being degraded, dispersed into particles and detached by tooth brushing.

11. The patch of claim 10, wherein the polymer having solubility parameter ($\delta 2$) of 23.5 $(MPa)^{1/2}$ to 40 $(MPa)^{1/2}$ is any one selected from polyalkyl vinyl ether-maleic acid copolymer, polyvinyl alcohol, polyacrylic acid, Poloxamer, polyethyleneoxide, polyvinyl pyrrolidone-vinyl acetate copolymer, polyvinyl pyrrolidone, polyquaternium-11, polyquaternium-39, carboxypolymethylene, hydroxypropyl methyl cellulose, hydroxyethyl cellulose, hydroxypropyl cellulose, gelatin, sodium alginate and a mixture thereof.

12. The patch of claim 10, wherein a weight ratio of the polymer having solubility parameter ($\delta 1$) of 5 $(MPa)^{1/2}$ to 22 $(MPa)^{1/2}$ and the polymer having solubility parameter ($\delta 2$) of 23.5 $(MPa)^{1/2}$ to 40 $(MPa)^{1/2}$ included in the backing layer is 1:0.2 to 4.0.

13. The patch of claim 1, wherein the backing layer includes a breakable portion.

14. The patch of claim 13, wherein the breakable portion includes prominence and depression or bubbles.

15. The patch of claim 14, wherein the prominence and depression have a concave portion in a depth of more than 0 μm and 30 μm or less based on a convex portion.

16. The patch of claim 14, wherein the prominence and depression have a concave portion in a width of more than 0 mm and 0.1 mm or less.

17. The patch of claim 10, wherein the backing layer has a static contact angle which varies over time.

18. The patch of claim 10, wherein the static contact angle varies from 13° to 50° over 10 sec to 300 sec when measured at a temperature of 20° C.

19. The patch of claim 10, wherein the backing layer has tensile strength reduction rate of 60% to 95%, compared to before moisture absorption.

20. The patch of claim 10, wherein the drug layer comprises at least one selected from the group consisting of an ingredient for whitening teeth, an ingredient for preventing or improving sensitive teeth, an ingredient for preventing cavities, and an ingredient for preventing periodontal disease.

* * * * *